United States Patent

Wunderlich et al.

[11] Patent Number: 6,103,269
[45] Date of Patent: Aug. 15, 2000

[54] SOLID BODIES CONTAINING ACTIVE SUBSTANCES AND A STRUCTURE CONSISTING OF HYDROPHILIC MACROMOLECULES, PLUS A METHOD OF PRODUCING SUCH BODIES

[75] Inventors: Jens-Christian Wunderlich, Heidelberg; Ursula Schick, Schriesheim; Jürgen Werry, Ludwigshafen; Jürgen Freidenreich, Schriesheim, all of Germany

[73] Assignee: Alfatec-Pharma GmbH, Heidelberg, Germany

[21] Appl. No.: 09/260,261

[22] Filed: Mar. 1, 1999

Related U.S. Application Data

[63] Continuation of application No. 08/256,578, Dec. 19, 1994, Pat. No. 5,876,754.

[30] Foreign Application Priority Data

Jan. 17, 1992 [DE] Germany ............................ 42 01 173
Jan. 17, 1992 [DE] Germany ............................ 42 01 179

[51] Int. Cl.[7] .................................. A61K 9/14; A61K 9/16
[52] U.S. Cl. ...................... 424/489; 424/439; 424/401; 424/450; 424/484; 424/490; 424/491; 424/493; 424/494; 424/497; 424/498; 514/772.3; 514/773; 514/774; 514/776; 514/777; 514/778; 514/779; 514/781; 514/782; 514/783; 514/784; 514/786; 514/937; 264/4.1; 264/4.33; 264/4.6; 264/13; 427/213.3; 427/213.33; 427/213.35; 427/213.36; 428/402.2; 428/402.21; 428/402.24
[58] Field of Search ................................ 424/489, 439, 424/401, 450, 484, 490, 491, 493, 494, 497, 498; 264/4.1, 4.33, 4.6, 13; 427/213.3, 213.33, 213.35, 213.36; 428/402.2, 402.21, 402.24

[56] References Cited

U.S. PATENT DOCUMENTS

| 4,412,986 | 11/1983 | Kawata et al. ............................ 424/80 |
| 4,540,602 | 9/1985 | Motoyama et al. ............... 427/213.31 |
| 4,758,598 | 7/1988 | Gregory .................................. 514/774 |
| 4,849,141 | 7/1989 | Fujioka et al. .......................... 264/207 |
| 5,019,400 | 5/1991 | Gombotz et al. ....................... 424/497 |
| 5,079,018 | 1/1992 | Ecanow .................................. 426/385 |

FOREIGN PATENT DOCUMENTS

| 71711/91 | 12/1990 | Australia . |
| 887901 | 1/1962 | United Kingdom . |

*Primary Examiner*—James M. Spear
*Attorney, Agent, or Firm*—Burns, Doane, Swecker & Mathis, L.L.P.

[57] ABSTRACT

The invention relates to accurately meterable shaped articles, for example granules or pellets, containing hydrophilic macromolecules, active compounds and optionally further pharmaceutically acceptable structure-forming substances and auxiliaries, the active compound being present in a matrix in dissolved, suspended or emulsified form, and a novel process for the production of these shaped articles, the process being particularly economically and ecologically acceptable, and use of the shaped articles as medicaments, in which the bioavailability, shelf life and tolerability is increased. Using the shaped articles or mixtures according to the invention, intermediates or final products for pharmacy, cosmetics, diagnosis, analysis or dietetics (healthcare) can additionally be advantageously prepared.

27 Claims, 2 Drawing Sheets

SOLID BODIES CONTAINING ACTIVE SUBSTANCES AND A STRUCTURE CONSISTING OF HYDROPHILIC MACROMOLECULES, PLUS A METHOD OF PRODUCING SUCH BODIES

This application is a continuation, of application Ser. No. 08/256,578, filed Dec. 19, 1994 U.S. Pat. No. 5,876,754.

The invention relates to accurately meterable powders, granules or pellets comprising hydrophilic macromolecules, active compounds and optionally other pharmaceutically acceptable structure-forming substances and auxiliaries, the active compound being dissolved, suspended or emulsified in a matrix, and a novel process for the production of these powders, granules or pellets, and furthermore their use as a medicament, cosmetic, diagnostic or dietetic foodstuff (healthcare). Active compounds employed are preferably dihydropyridine derivatives, in particular nifedipine, nitrendipine or nisoldipine.

Granules or pellets as shaped articles serve in the pharmaceutical industry mainly as intermediates for tableting. Shaping here should lead to a free-flowing, granular and dust-free product which, on account of its homogeneity, improves technological processing and dosage accuracy. Moreover, pellets, as a modern multiple-unit pharmaceutical form, for example filled into hard gelatin capsules, possess a number of advantages compared with single-unit pharmaceutical forms, such as e.g. tablets or coated tablets:

They disperse uniformly in the gastrointestinal tract.

On account of their small size shorter gastric residence times result in contrast to monolithic pharmaceutical forms, especially with enterically coated pharmaceutical forms.

As individual aggregates they dissolve more rapidly in the gastrointestinal tract in contrast to a compressed tablet, which must first disintegrate into its granule particles.

Pellets with differing release of active compound can be individually metered in mixed form.

However, the fundamental problem of the necessary shaping of pulverulent-crystalline active compounds and auxiliaries to processable granules (pellets) as shaped articles underlies all processes of the prior art.

A distinction is made here between building up and breaking down processes. It is common to all processes that until now granules or pellets as shaped articles were only obtained via various and complicated partial steps.

In the breaking down processes—presented in simplified form—the pharmaceutical substances and auxiliaries are first comminuted, brought to a uniform grain size by sieving and then mixed. Dry or moist granulation then takes place, in which the powder mixture is aggregated and then comminuted to give grains of granular material. In the next step, if necessary, it is dried and sieved again.

In the case of the building-up granules, grains of granular material are formed from the powdered pharmaceutical substances and auxiliaries with continuous addition of granulation fluid with simultaneous drying in a controlled process (e.g. fluidized bed process).

By means of subsequent, special rounding processes (e.g. Marumerizer®), round, bead-shaped granule particles (pellets) are obtained. A disadvantage in this case is that in the rounding of already prepared, un-shaped granule particles substance matter containing pharmaceutical substance is lost and cannot be directly fed to the granulation process again. This is certainly a problem in terms of cost and disposal. At the same time, the mechanical shaping leads to a non-uniform product.

Special pelleting techniques are, for example, build-up dry pelleting by compaction and fluidized bed granulation, which produce very unsatisfactory results with respect to shape and mechanical strength of the pellets.

All these preparation processes are technologically complicated multi-step processes. They are characterized by a multiplicity of process parameters of technological type, such as e.g. temperature, moisture content, homogeneity of the mixtures etc.

Furthermore, in all granulation and pelleting processes the use of a whole series of auxiliaries is necessary. Thus, for example, binders or granulation fluids must be employed to bring the powdered material into a solid, compact and processable form. The most accurate knowledge about the physicochemical behavior e.g. heat of solution, solubility or crystal formation tendency and great experience in working with these substances is necessary to be able to assess the interaction of these auxiliaries with one another and with the pharmaceutical substance in combination with all process parameters to be taken into account.

Thus the pharmaceutical requirements of granules (pellets) can often only be fulfilled by empirical tests depending on the pharmaceutical substance being processed and the administration form being formulated therefrom.

It is therefore understandable that the adherence to constant production conditions during the complicated process is very difficult. It is thus not possible, owing to the multiplicity of parameters to be taken into account, to find a suitable process for every pharmaceutical substance in the case of the known production processes despite a high outlay on development and optimization.

If pellets or granules prepared according to the prior art are moreover considered from biopharmaceutical aspects, it can be seen that the pharmaceutical substance from these aggregated shaped articles can be made available to the body only after deaggregation and subsequent release. The multiplicity of adhesive and binding forces, which differ in principle, in granules illustrates this problem. As a result of hardening binders during drying (moist granulation) or as a result of sintering or melt adhesion under action of pressure (dry granulation) solid bridges form whose binding forces in the body must be overcome first in order to release the pharmaceutical substance from the pharmaceutical form at all.

Each preparation step in the processes of the prior art can thus have an unfavorable effect on the release of the active compound and thus on its bioavailability.

Looked at pharmacologically, dihydropyridine derivatives are amongst the calcium antagonists. They are indicated in a number of cardiovascular disorders, such as e.g. coronary heart disease, arterial hypertension, angina pectoris etc. The prescription frequency of about 700 million defined daily doses in 1989 very clearly confirms the market position of this substance group. The first representative of this group of dihydropyridine derivatives, nifedipine (dimethyl 1,4-dihydro-2,6-dimethyl-4- (2-nitrophenyl)pyridine-3,5-dicarboxylate, $C_{17}H_{18}N_2O_6$) was supplemented in the meantime by a number of potent derivatives, the so-called "second-generation dihydropyridines", particularly nitrendipine, ethyl methyl 1,4-dihydro-2,6-dimethyl-4-(3-nitrophenyl)-pyridine-3,5-dicarboxylate, $C_{18}H_{20}N_2O_6$ and nisoldipine, isobutyl methyl 1,4-dihydro-2,6-dimethyl-4-(2-nitro-phenyl)pyridine-3,5-dicarboxylate, $C_{20}H_{24}N_2O_6$.

The dosage of commercially available nifedipine immediate-effect medicaments when given in a single dose is customarily 5–10 mg; more recent dihydropyridine derivatives are in some cases given at a lower dose.

In order to bring dihydropyridines, particularly nifedipine, into an administration form which releases the active compound sufficiently rapidly in the body, pharmaceutical formulation developments have frequently been proposed. These, however, are all compromises, because on the one hand the poor solubility or insolubility of these active compounds in the physiological medium restricts or makes difficult their rapid release from pharmaceutical forms. On the other hand, the rapid release, however, is a prerequisite for an onset of action after administration which is as rapid as possible. These processes are not unimportant for increasing patient compliance.

Conventional, technological methods in the preparation of immediate-effect pharmaceutical forms of dihydropyridine derivatives, particularly nifedipine, are the following:

a) processing of the active compounds with solubilizers (surfactants) and additionally
b) dissolution of the active compounds in organic solvents, e.g. polyether alcohols of tetrahydrofurfuryl alcohol.

Because of the known light sensitivity of the dihydropyridines, a conventional, colored soft gelatin capsule may be used e.g. as a carrier (light protection) for an abovementioned nifedipine solubilizate or a nifedipine solution in an organic solvent. After administration, the nifedipine should be released from the pharmaceutical form in fine form. It is to be considered here, however, that the active compound is then not actually free, but must first be released from its complex with the solubilizer, with the disadvantage that it is not sufficiently rapidly available to the body. Additionally, there is also always the risk in this process that nifedipine precipitates under physiological conditions in relatively coarse crystalline form as soon as the solubilizer (surfactant) is no longer active. Moreover, the use of surfactants or organic solvents is not completely safe from toxicological considerations.

Liquid nifedipine preparations able to form drops are also commercially available. For the patient, these nifedipine drops are a very popular administration form, particularly for elderly patients who find the swallowing of solid shaped articles (tablets, capsules) unpleasant or have difficulties with it. Moreover, they have the advantage of good meterability.

Although liquid pharmaceutical preparations, looked at technologically, are actually well conceived immediate-effect pharmaceutical forms (the process of the disintegration of solid, "single-unit" forms such as, for example, tablets or capsules does not apply), these preparations are not in keeping with the times in the case of the dihydropyridines on the one hand for the reasons already mentioned above (use of surfactants and/or organic solvents), and on the other hand for a further, even more far-reaching reason which is to be sought in this class of active compound itself. As is known, dihydropyridines are highly light-sensitive and tend to decompose, in particular in solutions.

Partial decomposition of the nifedipine as a result of admission of light, even before taking, is therefore never to be excluded particularly during withdrawal of nifedipine drops from the storage container by the patient. Since this form of administration, particularly in the case of elderly patients, is a very time-consuming process, the risk of decomposition of active compound before actual administration is thus additionally increased.

It is further to be taken into consideration that even the storage of nifedipine drop solutions in brown or dark-colored glass bottles may not offer adequate, relatively long storage stability (protection from admission of light!).

For dihydropyridine derivatives administration as an immediate-effect form having a rapid influx, the preparation itself being an active compound solution, is desirable or advantageous from pharmacological considerations. However, owing to the physicochemical properties of the active compound, such as, for example, inadequate water solubility, light sensitivity in solution etc., this administration form cannot be realized technologically or can only be realized in a roundabout manner.

The present invention has the object of proposing novel solids, a process for their production, and mixtures which on the one hand on account of their structure and composition improve the bioavailability and tolerability of pharmaceutical substances, are stable on storage, accurately meterable and present as a single or multiple unit and on the other hand can be prepared in an environmentally protective, simple and economical manner, process the active compounds in a gentle manner and thus, looked at all together, overcome the disadvantages of the prior art.

The present invention is in particular based on the object of providing a medicament for oral administration of dihydropyridine derivatives, particularly nifedipine, which is suitable for rapid pharmaceutical substance release and overcomes the problems of the prior art.

This object is achieved according to the invention by active compound-containing solids which comprise the pharmaceutical substance in dissolved, emulsified or suspended form in a solid or semisolid matrix which mainly contains hydrophilic macromolecules of natural origin as structure-forming agents.

The hydrophilic macromolecules employed are:
collagen, gelatin, fractionated gelatin, collagen-hydrolyzates, gelatin derivatives, plant proteins, plant protein hydrolyzates, elastin hydrolyzates and combinations of the abovementioned substances with one another.

In particular, the present invention makes available active compound-containing solids which comprise a dispersion of at least one active compound or active compound mixture in a matrix which essentially includes a structure-forming agent comprising hydrophilic macromolecules selected from the group consisting of:
collagen, gelatin, fractionated gelatin, collagen hydrolyzates, gelatin derivatives, plant proteins, plant protein hydrolyzates, elastin hydrolyzates and mixtures of the abovementioned substances.

This object is further achieved by a process for the production of active compound-containing solids which comprises dissolving, emulsifying or suspending the active compound in a solution of the hydrophilic macromolecule (structure-forming agent) and shaping to give shaped articles.

The solids can be dried if required.

In particular, the present invention makes available a process for the production of solids containing at least one active compound, which comprises a) dissolving a structure-forming agent comprising hydrophilic macromolecules selected from the group consisting of:
collagen, gelatin, fractionated gelatin, collagen hydrolyzates, gelatin derivatives, plant proteins, plant protein hydrolyzates and elastin hydrolyzates in an aqueous and/or organic solvent,
b) dispersing the active compound,
c) adding the mixture of dissolved structure-forming agent and dispersed active compound obtained dropwise to a deep-cooled liquid and thus shaping the solid.

Solid within the meaning of the invention is understood as meaning one which is selected from the group consisting of:

powders, granules, pellets and micropellets in essentially symmetrically built-up aggregates.

According to the invention, uniformly round solids, in particular pellets, are particularly suitable for pharmaceutical applications, the term pellet preferably comprising a grain size range from about 0.2 to 12 mm.

In the description of the invention the properties, preparation and use are preferably presented with the aid of round pellets.

However, the person skilled in the art can also employ other solids from the group consisting of: powders, granules, essentially symmetrically built-up aggregates, advantageously for the production, in particular, of pharmaceutical forms.

In addition, the object of the present invention is achieved by a mixture which contains at least one active compound and a structure-forming agent wherein the structure-forming agent is a hydrophilic macromolecule selected from the group consisting of:
collagen, gelatin, fractionated gelatin, gelatin derivatives, collagen hydrolyzates, plant proteins, plant protein hydrolyzates, elastin hydrolyzates, albumins, agar-agar, gum arabic, pectins, tragacanth, xanthan, natural and modified starches, dextrans, dextrins, maltodextrin, chitosan, alginates, cellulose derivatives, polyvinyl alcohol, polyvinylpyrrolidone, polyacrylic acid and polymers of methacrylic acid and methacrylic acid esters; and their mixtures.

The active compound used according to the present invention is preferably a dihydropyridine derivative, in particular nifedipine, nitrendipine or nisoldipine.

Preferred embodiments of the invention are described and claimed in the dependent claims.

The solid to semisolid or gelatinous pellets according to the invention are round, uniform shaped articles in the range from 0.2–12 mm. Pellets in the range from 0.2–2 mm are suitable for multiple unit dosage forms, pellets in the range from 2–12 mm can be used as a single unit dosage form.

With respect to medicament safety, exact dosage accuracy, homogeneity, tolerability and storage stability of the corresponding pharmaceutical form are required by the pharmaceutical industry. With conventional medicament production, this standard is often only to be achieved with a high and cost-intensive outlay. The uniform grain size distribution of the claimed pellets, combined with a homogeneous dispersion of the pharmaceutical substance, improves the dosage accuracy distinctly compared with the prior art. Furthermore, the active compounds embedded in the pellet matrix are brought into a storage-stable form which has a high mechanical strength with low friability. Sensitive active compounds are additionally reliably protected from external effects.

As shaped articles, the pellets according to the invention, which are distinguished by their homogeneous round and uniform shape, are visually very attractive on account of their harmonic total impression and can increase acceptance in the patient. By means of appropriate coloring, the pellets, which appear clearly transparent and lustrous, opaque to transparent or non-transparent, can be developed to give unmistakable pharmaceutical specialties.

As a result of the advantageous protective colloid function of the claimed macromolecules and the simultaneous embedding of the active compounds in the polymeric matrix structure, the tolerability is distinctly increased, in particular in the case of mucous membrane-irritating active compounds. Thus e.g. the irritation of the gastric mucous membrane by acetylsalicylic acid can be effectively decreased by the mucous membrane-protective action of the claimed macromolecules (cf. Example 7). As a pharmaceutical form, the pellets described are palatable and easy to take orally.

Surprisingly, the release of the active agent takes place in the body without an advance disintegration process in all pharmaceutical substances independently of whether they are dissolved, suspended or emulsified in the pellets according to the invention as shaped articles, in contrast to conventional granules, pellets or tablets. In conventional preparations, the adhesive and binding forces which make possible shaping at all must initially be overcome, in addition the subaggregates thus obtained must be wetted and dissolved until the pharmaceutical substance is finally in an absorbable form. Depending on the nature of the auxiliaries used and the preparation process used, conventional solid pharmaceutical forms can reduce the bioavailability of active compounds significantly.

The dissolution process from the pharmaceutical form as a time-determining factor depends in the case of the pellets according to the invention as shaped articles exclusively on the nature and composition of the hydrophilic matrix system and can be modulated in the release rate. Immediate-effect forms which dissolve within a few seconds can thus be formulated even as sustained-release forms. The dissolution of the structure-forming agent is the rate-determining step.

In the case of hydrophobic or poorly soluble pharmaceutical substances, the hydrophilic macromolecules described improve the absorption or the bioavailability and can be coordinated according to the invention with the particular pharmaceutical substance with respect to physicochemical and pharmaceutical properties.

In the case of pharmaceutical substances which under conventional conditions count as being poorly absorbable or having problematic bioavailability, a bioavailability increase of up to 100 to 150% can thus be achieved by incorporation, even as a simple dispersion, into a preparation according to the invention, in comparison with a conventional preparation of the same dose of the pharmaceutical substance.

Obviously, the presence in a preparation according to the invention thus leads to a greatly increased (more effective) absorption of the pharmaceutical substance dose under physiological conditions.

The pharmaceutical substance-containing pellets are exposed during the gentle preparation process (shaping) to low temperatures and only come into contact with an inert medium (liquid nitrogen). Alteration of the pharmaceutical substances or contamination with residues of cooling oils or organic solvents, such as is known, for example, of the classical soft gelatin capsule preparation, therefore does not take place.

From technological and biopharmaceutical aspects, the pellets described in principle fulfill all requirements which are to be made of this dosage form:
they are uniform in shape and color,
possess a narrow grain size distribution,
can be easily metered and filled,
have a high mechanical strength and shelf life,
release the pharmaceutical substance rapidly or in a modulated manner.

Within the meaning of the invention—on their own or in mixtures—hydrophilic macromolecules from the group consisting of:
collagen, gelatin, fractionated gelatin, gelatin derivatives, collagen hydrolyzates, plant proteins, plant protein hydrolyzates and elastin hydrolyzates can be employed.

These biogenic substances are pharmaceutically acceptable and non-toxic. The matrix properties of said proteins can be adjusted within wide limits with accurate knowledge of their physicochemical behavior and thus lead to a medicament in which the respective active compound is present in optimum and reproducible form.

Gelatin is a scleroprotein obtained from collagen-containing material, which has different properties depending on the preparation process. It consists essentially of four molecular weight fractions which affect the physicochemical properties as a function of molecular weight and percentage weight content. The higher e.g. the content of microgel ($10^7$ to $10^8$ D), the higher also the viscosity of the aqueous solution. Commercially available types contain up to 10 percent by weight. The fractions of alpha-gelatin and its oligomers ($9.5 \times 10^4/10^5$ to $10^6$ D) are crucial for the gel solidity and are customarily between 10 and 40 percent by weight. Molecular weights below that of alpha-gelatin are designated as peptides and can amount to up to 80 percent by weight in conventional grades of gelatin (low-Bloom).

Gelatin possesses a temperature—and concentration-dependent reversible sol/gel conversion behavior which is dependent on the molecular composition. As a measure of the gel formation power of the gelatin, it is internationally customary to give the Bloom number. Low commercially available grades start at 50 Bloom, high-Bloom types are about 300 Bloom.

The chemical and physical properties vary depending on the preparation process, particularly gently obtained types of gelatin (low content of dextrorotatory amino acids and peptides) having short sol/gel conversion rates and melting points above 37° C. (measured as a 10% strength solution).

Fractionated gelatin represents the special case of gelatin and is obtained from conventional gelatin by special preparation techniques, such as e.g. ultrafiltration. The composition can be varied e.g. by removal of peptides (MW<$9.5 \times 10^4$ D) or by mixtures of individual fractions such as e.g. alpha chains, dimeric and trimeric chains or microgel.

Moreover, gelatin or fractionated gelatin has good surfactant properties with protective colloid action and emulsifying properties.

Collagen in native form is water-insoluble. By means of special preparation processes there are today soluble types of collagen having an average molecular weight of about 300,000 D.

Gelatin derivatives are chemically modified gelatins, such as e.g. succinylated gelatin, which are used e.g. for plasma expanders.

Collagen hydrolyzate is understood as meaning a product obtained from collagen or gelatin by pressure hydrolysis or enzymatically which no longer has sol/gel conversion power. Collagen hydrolyzates are readily cold water-soluble and the molecular weight composition can be between a few hundred D to below $9.5 \times 10^4$ D. Products obtained by enzymatic routes are more homogeneous in molecular composition and additionally exhibit good surfactant and emulsifier action.

The plant proteins and their hydrolyzates are newly developed products, which largely correspond to the collagen hydrolyzates in their properties. They are preferably obtained from wheat and soybeans and possess, for example, molecular weights of about 200,000–300,000 D and about 1,000–10,000 D respectively.

Elastin hydrolyzates are obtained enzymatically from elastin and consist of a single polypeptide chain. On account of their high content of non-polar amino acids they can be used in lipophilic systems. Elastin hydrolyzates have a molecular weight of about 2,000–3,000 D and have great film-forming power on the skin.

When using vegetable proteins, plant protein hydrolyzates, elastin hydrolyzates, or collagen hydrolyzates (cold water-soluble gelatirs) or gelatins having a maximum in the molecular weight distribution of a few hundred D to below $10^5$ D (variant A), the excipient material of the claimed shaped articles after lyophilization carried out in a preferred embodiment of the invention surprisingly forms a highly porous and at the same time mechanically stable matrix which dissolves rapidly and completely in cold water.

If the pharmaceutical substance is present in the matrix in dissolved or suspended form, all said hydrophilic macromolecules in the indicated molecular weight ranges are suitable according to the invention on their own or in mixtures. Emulsified pharmaceutical substances having rapid release are advantageously prepared by use of collagen hydrolyzates with still present surfactant and emulsifier properties. Enzymatically obtained hydrolyzates which have a molecular weight between about 15,000 and 20,000 D are particularly suitable.

The rapid dissolution of the matrix recipes described is suitable for pharmaceutical immediate-effect forms in which the active compound can be present in a single or multiple dose.

For internal administration, instant preparations can advantageously be formulated from the pellets according to the invention as shaped articles. If e.g. the active compound is embedded in a rapidly dissolving matrix and pelletized, storage-stable pellets are obtained which (e.g. filled into a sachet) can be dissolved completely in cold water within a few seconds.

According to the invention, hydrophilic macromolecules with sol/gel-forming properties such as e.g. gelatin and fractionated gelatin, which possess a maximum in the molecular weight distribution above $10^5$ D, may also be suitable as structure-forming substances.

If the pharmaceutical substance is present in dissolved, suspended or emulsified form in a sol/gel-forming structural matrix (variant B) such as gelatin or fractionated gelatin, pellets are obtained which release the active compound—depending on the molecular composition of the type of gelatin used—rapidly or slowly in aqueous medium at 37° C.

In a further embodiment of the invention, additions of plasticizers of 1–50% (relative to the material to be processed) selected from the group consisting of: glycerol, propylene glycol, polyethylene glycols, triacetin, sorbitol, sorbitan mixtures, sorbitol solutions, glucose syrup and other polyols or sugar alcohols, may be suitable. Said substances affect the matrix according to the invention with respect to consistency from solid to semisolid or gelatinous, its dissolution behavior and the viscosity. A particularly advantageously suitable plasticizer is sorbitol, which as a sweetener with non-cariogenic properties simultaneously serves as a flavor correctant.

In a particular embodiment of the invention, pellets comprising matrix materials with plasticizer additions of 20 to 50% (relative to the material to be processed) have pronounced bioadhesive properties.

Furthermore, it may be desirable to add to the described matrix materials lipophilic constituents, such as e.g. phospholipids for the formation of liposomes.

For pellets as shaped articles which dissolve in water at 37° C. within a few minutes, types of gelatin are preferably selected whose peptide content is above 30% and which have a maximum in the molecular weight distribution at about $10^5$ D to $10^6$ D.

For the formulation of pellets having properties which delay release, types of gelatin having a peptide content of below 10% and a microgel content of 10–15% are suitable within the meaning of the invention. Matrix materials or mixtures built up in this way possess a melting range from 35° C. to 40° C., preferably above 37° C., in aqueous solution. Addition of plasticizers may be in the range between 1 and 30% (relative to the material to be processed).

The following can be employed as additional structure-forming agents of 1–50% (relative to the material to be processed): albumins, agar-agar, gum arabic, pectins, tragacanth, xanthan, natural and modified starches, dextrans, dextrins, maltodextrin, chitosan, alginates, alginate-calcium phosphates, cellulose derivatives, polyvinyl alcohol, polyvinylpyrrolidone, polyacrylic acid and polymers of methacrylic acid and methacrylic acid esters.

Celluloseacetate phthalate or hydroxypropylmethylcellulose phthalate, azo-crosslinked polymethacrylate; polyurethane/sugar copolymers, a suitable sugar component in particular being oligomeric galactomannans or galactomannan derivatives which are then crosslinked with aliphatic diisocyanates; galactomannan derivatives such as ethyl- or acetylgalactomannans; polysaccharides crosslinked with adipic acid, lipophilic substances such as degradable mono-, di- and triglycerides; and erodable fatty alcohols.

In a further embodiment of the invention, 1–50% strength additions of substances can be selected from this group in order to suit the physical or chemical properties of the matrix, such as e.g. the viscosity, the mechanical strength or the dissolution properties of the polymeric structure, to the active compound and the intended use. Thus, for example, using substances such as dextrans, modified starches, sugars and in particular mannitol, pellets according to the invention can be prepared which as a lyophilizate form a highly porous network. Macromolecules such as e.g. alginates, agar-agar and pectins can be used according to the invention for the additional retardation or modification of the release of active compound.

To this groundmass can be added further auxiliaries and excipients suitable for pharmaceutical use, such as e.g. fillers, such as e.g. lactose, dispersants, such as e.g. disodium phosphate, pH correctants, such as e.g. disodium citrate, emulsifiers, such as e.g. lecithin, stabilizers, such as e.g. ascorbic acid, cosolvents, such as e.g. polyethylene glycol, natural colorants, such as e.g. carotenoids, aromatizing substances or flavor correctants, such as e.g. sugar substitutes, complex-forming agents or inclusion complex-forming agents, such as e.g. cyclodextrin.

In a particular embodiment of the matrix materials or mixtures indicated in variants A and B, which can be built up with or without addition of plasticizer, pellets can be prepared by addition of enteric-resistant substances from the group: poly- and methacrylic acid derivatives, cellulose derivatives and their mixtures, which release the pharmaceutical substance only after gastric passage, i.e. that the structure-forming agent of the matrix mixture dissolves in a predetermined pH range.

Instead of the abovementioned enteric-resistant substances, substances can also be used which are only degraded after reaching a certain section of the intestine by enzymes present there. These are e.g. azo-crosslinked polymethacrylates; polyurethane/sugar copolymers, a suitable sugar component in particular being oligomeric galactomannans or galactomannan derivatives which are then crosslinked with aliphatic diisocyanates; galactomannan derivatives such as ethyl- or acetylgalactomannans; polysaccharides crosslinked with adipic acid.

Pellets according to the invention can be prepared in this manner which are particularly suitable for colonic pharmaceutical forms. After reaching the colon, a pellet matrix of this type is degraded enzymatically and the incorporated pharmaceutical substance thus released in a controlled manner in this gastrointestinal section.

Further embodiments to colonic pharmaceutical forms are found in particular in the international PCT application titled "Peptidarzneistoffe enthaltende Formkörper und ihre Herstellung sowie deren Verwendung" (Shaped articles containing peptide pharmaceutical substances, their preparation and their use) of ALFATEC-Pharma GmbH of the same date.

In the case of alginate-containing basic recipes, by suspending water-insoluble dicalcium hydrogen phosphate $[(Ca_2(HPO_4)_2]$ e.g. to give a pH-neutral to slightly basic gelatin/alginate mixture pellets can be produced which have delayed release of the active compound. During gastric passage, the acidic medium dissolves the calcium salt and crosslinks the alginate.

Furthermore, pharmaceutically acceptable hardeners, such as e.g. aldoses or citral, which after drying lead to crosslinking, can be added according to the invention to the structure-forming substances derived from collagen.

A suitable hardener is in particular xylose, as it makes possible a specifically controllable crosslinking of the pellet matrix. In this manner depot pharmaceutical forms, so-called sustained-release pharmaceutical forms, can be realized, it being possible according to the invention to set different release characteristics of the pharmaceutical substance with high reproducibility.

This modulation of pharmaceutical substance release is seen particularly clearly if the behavior of a crosslinked matrix of this type is looked at in aqueous medium. The pellets no longer dissolve in aqueous medium, on the contrary as a result of crosslinking (derivatization of the structure-forming agent) they show a more or less highly pronounced swelling behavior. This swelling behavior is now adjustable in a controlled manner via the amount of crosslinking agent added, i.e. by the extent of hardening or via the selected hardening conditions. Different molecular fractions of a structure-forming agent derived from collagen can in this way be crosslinked very specifically and with high reproducibility.

On the one hand, pharmaceutical substance release profiles can thus be achieved according to the invention which correspond to the conventional diffusion from matrix formulations (square root law, compare Higuchi equation).

On the other hand, however, which is all the more surprising, using the same starting materials (structure-forming substances and crosslinking agents) a pharmaceutical substance release profile of zero order (linear kinetics) can also be reproducibly established. In this special case a non-Fick's diffusion from the matrix can be assumed, i.e. a swelling-controlled diffusion with a transition from a vitreous matrix to a swollen matrix, the diffusion coefficient of the pharmaceutical substance in the matrix itself gradually increasing during the swelling process. Intermediate states between the two release profiles shown can also be established.

As the pellets according to the invention, as shaped articles, possess high mechanical stability, they can be coated with pharmaceutically customary film-forming agents. The desired absorption section in the gastrointestinal tract can be specifically reached particularly advantageously by combination of matrix materials, which in particular have bioadhesive properties, and film coatings (e.g. poly- and methacrylic acid derivatives) which dissolve in defined pH ranges.

Such bioadhesive properties can be produced, for example, by partial crosslinking of a matrix which is constructed from an auxiliary derived from collagen.

Instead of Eudragits® suitable film coatings made of substances which after reaching the colon are degraded by enzymes present there can also be employed. These are e.g. azo-crosslinked polymethacrylates; polyurethane/sugar copolymers, a suitable sugar component in particular being oligomeric galactomannans or galactomannan derivatives which are then crosslinked with aliphatic diisocyanates; galactomannan derivatives such as ethyl- or acetylgalactomannans; polysaccharides crosslinked with adipic acid.

This procedure makes possible the absorption of pharmaceutical substances with problematic bioavailability in a controlled manner. Furthermore, by combinations of film-forming agents, pellet mixtures can be prepared according to the invention which release the active compound from the pharmaceutical form in a pulsed manner.

The already mentioned bioavailability increase achievable according to the invention is surprisingly also provided in the case of controlled crosslinking of a pellet matrix. According to the invention, pellet pharmaceutical forms with modulated or pulsed pharmaceutical substance release can thus be advantageously prepared with retention of the increased bioavailability of the pharmaceutical substance.

As is known, gelatin, depending on the preparation process, possesses an isoelectric point in the acidic (gelatin type B) or in the alkaline range (gelatin type A). This property is utilized according to the invention for the direct formation of micro- or nano-capsules in the matrix material. Thus, when using gelatins of opposite charge mixed with active compound-containing solution (e.g. at a pH of 6–7), microcapsules can be prepared by removing the solvent. When using types of gelatin or collagen derivatives having defined molecular composition, three-dimensional crosslinkings in the nanometer range can be carried out. Gelatins or collagen hydrolyzates can furthermore form conjugates with the active compound e.g. with an about 2–3% strength addition of salts.

The bioavailability increase of pharmaceutical substances according to the invention described at the beginning can surprisingly even be achieved if a pharmaceutical substance is present dispersed in a pellet matrix in coarsely disperse form.

When using micronized powders which are present dispersed in a pellet matrix according to the invention, a distinct bioavailability increase again results in comparison with a conventional suspension of a micronized powder. Thus, in example 8 an immediate-effect pharmaceutical form on a pellet basis is described which contains ibuprofen. The bioavailability of this pellet preparation compared with a conventional, orally administered suspension of micronized ibuprofen is increased by about 100% to 150% at the same dose. Obviously, the presence of a pharmaceutical substance in a preparation according to the invention advantageously leads to a greatly increased (more effective) absorption of the pharmaceutical substance under physiological conditions.

Active compounds having problematic bioavailability can be brought according to the invention in a further development form into a finely disperse form promoting absorption by direct and controlled precipitation of the active compound previously present in the matrix material in dissolved form, e.g. by pH shift or removal of the solvent.

Suitable particularly finely disperse pharmaceutical substance dispersions are colloidally disperse pharmaceutical substance systems (nanosols) whose properties and preparation are described in numerous patent applications of ALFATEC-Pharma GmbH (e.g. PCT Application PCT/DE92/01010 and further PCT applications cited there).

Pharmaceutically customary organic solvents and cosolvents which are preferably miscible in aqueous solution can be added to the claimed matrix materials if the active compound is water-insoluble.

By the combination of pellets which contain active compounds from different indication groups, combination preparations can be obtained, eg. by filling in customary hard gelatin capsules. Useful combinations may be, for example: dihydrbpyridine derivative+beta-sympathicolytic or diuretic.

Other intended uses are eg. filling into sachets to give beverage granules (beverage pellets) or use for the preparation of initial doses in depot pharmaceutical forms etc.

Starting from a single product—the shaped articles according to the invention—a considerable technological breadth of application is thus provided.

In the following, the process for the preparation of the pellets according to the invention is described in greater detail.

Further embodiments to this are contained in the parallel international (PCT) applications listed in the following. The contents of these parallel PCT applications, filed on the same date at the German patent office by the same inventors and applicants:

internal reference: P/81AL2740, Title: "flanzenextrakt(e) enthaltende Formkörper, insbesondere Pellets und ihre pharmazeutische oder kosmetische Verwendung", (Shaped articles containing vegetable extract(s), in particular pellets, and their pharmaceutical or cosmetic use),
  PCT/DE93/
    claimed Priorities:
      German patent application P 42 01 179.5 of Jan. 17, 1992, U.S. Ser. No. 07/876,876 of Mar. 30, 1992, U.S. Ser. No. 07/876,866 of Apr. 30, 1992 and German patent application P 42 01 172.8.
  internal reference: P/81AL2742, Title: "Verfahren zur Herstellung von Weichgelatinekapseln nach einem Tropfverfahren", (Process for the production of soft gelatin capsules by a drip-feed process),
  PCT/DE93/
    claimed Priorities:
      German patent application P 42 01 178.7 of Jan. 17, 1992 and U.S. Ser. No. 07/876,863 of Apr. 30, 1992
  internal reference: P/81AL2743, Title: "Peptidarzneistoffe enthaltende Pellets und ihre Herstellung sowie deren Verwendung" (Pellets containing peptide pharmaceutical substances, their production and their use)
  PCT/DE93/
    claimed Priorities:
      German patent application P 42 01 179.5 of Jan. 17, 1992 and U.S. Ser. No. 07/876,865 of Apr. 30, 1992
  are hereby also made a part completely in terms of contents for the disclosure of the present application, like the earlier PCT applications:
  PCT/DE92/01010, PCT/DE92/01012, PCT/DE92/01014,
  PCT/DE92/01016, PCT/DE92/01007, PCT/DE92/01008,
  PCT/DE92/01015, PCT/DE92/01013, PCT/DE92/01009,
  PCT/DE92/01011 of 12.4.1992.

In the simplest case, the process according to the invention for the production of active compound-containing solids can be described by the following three process steps:

a) a structure-forming agent comprising hydrophilic macromolecules is dissolved in a solvent, b) the active compound is dispersed in this solution and c) the mixture of dissolved structure-forming agent and dispersed active compound obtained is added dropwise to a deep-cooled inert liquefied gas and the solid is thus formed.

The first step of the process consists in dissolving the hydrophilic macromolecule, in particular gelatin, fractionated gelatin, collagen hydrolyzates or gelatin derivatives or alternatively mixtures of macro-molecular substances, in a suitable solvent—water as a solvent is the choice to be preferred in most cases. The use of heat may be necessary here, such as e.g. with gelatin a temperature of 37° C. or more, in order to obtain a gelatin sol.

Further auxiliaries and excipients, such as e.g. fillers, such as e.g. lactose, dispersants, such as e.g. disodium hydrogen phosphate, pH correctants, such as e.g. disodium citrate, emulsifiers, such as e.g. lecithin, stabilizers, such as e.g. ascorbic acid, cosolvents, such as e.g. polyethylene glycol, natural colorants, such as e.g. carotenoids, aromatizing substances or flavor correctants, such as e.g. sugar substitutes, complex-forming agents or inclusion complex-forming agents, such as e.g. cyclodextrin are added.

Concentration ranges of the hydrophilic macromolecules, in particular gelatin, collagen hydrolyzates or gelatin derivatives are preferably below 30% (% by weight), e.g. in the range from 3–15%, relative to the material without active compound to be processed. Correspondingly the water content of the material to be processed is up to about 70% by weight or more.

Concentration ranges of the additional structure-forming agents, such as, for example, dextrans, sucrose, glycine, lactose, polyvinylpyrrolidone, but in particular mannitol, are below 30% (% by weight), e.g. in the range from 0–15%, relative to the material without active compound to be processed. Preferably the content of additional structure-forming agent is not greater than the content of the actual structure-forming agent.

As filler components, these substances, in particular mannitol, however, can improve the stability of the polymeric structure in the pellets according to the invention and thus also its mechanical properties.

In the second step the dihydropyridine derivative is dispersed in as finely divided a form as possible in the solution of the hydrophilic macromolecule.

The system described in the second step is then added dropwise to a deep-cooled, easily evaporable liquid in the third step for shaping via a suitable metering system, preferably in an immersion bath containing liquid nitrogen. Each discrete drop in this process assumes spherical shape, on the one hand even during free fall, on the other hand in the immersion bath as a result of the gas envelope formed around it or the system/gas interfacial tension, before complete freezing takes place. Precisely this rapid, but still controllably manageable freezing fixes the given state of the system instantly, i.e. no pharmaceutical substance can diffuse into the surrounding medium, dissolved pharmaceutical substance can no longer crystallize out, suspensions can no longer sediment, emulsions can no longer break, thermally sensitive or moisture-sensitive substances are cryopreserved, the excipient structure cannot contract, etc. The preparation process using an inert liquid gas thus has no disadvantageous effect on or change in the product as a consequence, which is a great advantage. The desired properties are maintained.

In an embodiment of the process step described in a), a material capable of forming drops, mainly comprising hydrophilic macromolecules as structure-forming agents, in particular plant proteins, plant protein hydrolyzates, collagen, gelatin, fractionated gelatin, elastin hydrolyzates, collagen hydrolyzates, gelatin derivatives or mixtures of the abovementioned substances, and the active compound is prepared.

The active compound is initially dispersed, i.e. dissolved, suspended or emulsified, e.g. in the structure-forming agent present in dissolved form, in particular plant proteins, plant protein hydrolyzates, collagen, gelatin, fractionated gelatin, gelatin derivatives, collagen hydrolyzates or elastin hydrolyzate, the nature and amount of the structure-forming agent employed and optionally the addition of further auxiliaries depending on the later intended use of the shaped article. The concentration of the excipient material may vary, for example, from 0.5 to 60% (g/g), preferably 0.5 to 30% (relative to the material to be processed). The use of heat in the temperature range from about 30° C. to 60° C., preferably about 45° C., may be necessary e.g. when using gelatin in order to convert this into the sol form.

Addition of additional structure-forming agents of from 1–50% (relative to the material to be processed) selected from the group consisting of: albumins, agar-agar, gum arabic, pectins, tragacanth, xanthan, natural and modified starches, dextrans, dextrins, maltodextrin, chitosan, alginates, cellulose derivatives, polyvinyl alcohol, polyvinylpyrrolidone, polyacrylic acid and polymers of methacrylic acid and methacrylic acid esters, cellulose acetate phthalate or hydroxypropylmethyl-cellulose phthalate, azo-crosslinked polymethacrylates; polyurethane/sugar copolymers, a suitable sugar component in particular being oligomeric galactomannans or galactomannan derivatives which are then crosslinked in the aliphatic diisocyanates; galactomannan derivatives such as ethyl- or acetylgalactomannans; polysaccharides crosslinked with adipic acid; lipophilic substances such as degradable mono-, di- and triglycerides; and erodable fatty alcohols can furthermore be added to the matrix material.

In a further process variant, additions of plasticizers of from 1–50% (relative to the material to be processed) may be added selected from the group consisting of: glycerol, propylene glycol, polyethylene glycols, triacetin, sorbitol, sorbitan mixtures, sorbitol solutions, glucose syrup and other polyols or sugar alcohols.

Further auxiliaries and excipients suitable for pharmaceutical use, such as e.g. fillers, such as e.g. lactose, dispersants, such as e.g. disodium hydrogen phosphate, pH correctants, such as e.g. disodium citrate, emulsifiers, such as e.g. lecithin, stabilisers, such as e.g. ascorbic acid, cosolvents, such as e.g. polyethylene glycol, natural colorants, such as e.g. carotenoids, aromatizing substances or flavor correctants, such as e.g. sugar substitutes, complex-forming agents or inclusion complex-forming agents, such as e.g. cyclodextrin can be added to this groundmass.

Of course, the mixtures according to the invention are suitable for immediate filling in liquid form according to the process step described in a) for shaping in containers, such as e.g. molds, soft gelatin capsules and suitable other coverings.

In one embodiment of the process step described in b), the matrix material described is added dropwise for rounding (shaping) and shock deep-freezing in an immersion bath in the range from about −70° C. to about −270° C., preferably from about −100° C. to −220° C. The deep-cooled, in particular inert, liquid employed is preferably liquid nitrogen, which does not alter the constituents of the pelets. Round shaped articles (pellets) which after drying form a mechanically stable matrix are formed in the deep-cooled liquid. Shaping is carried out by means of a suitable metering system. Each discrete drop in this process assumes spherical shape, on the one hand even during free fall, on the other hand in the immersion bath as a result of the gas envelope formed around it or the system/gas interfacial tension in the immersion bath, before complete freezing takes place. Precisely this rapid, but still controllably manageable freezing fixes the given state of the system instantly, i.e. no active compounds can diffuse into the surrounding medium, dissolved constituents can no longer crystallize out, suspensions can no longer sediment, emulsions can no longer break, thermally sensitive or moisture-sensitive active compounds are cryopreserved, and the excipient structure cannot contract, etc. The preparation process using an inert liquid gas thus has no disadvantageous effect on or change in the active compound or the matrix material as a consequence. The retention of the desired properties is thus of particular advantage. Furthermore the process operates without solvents, does not pollute the environment and can be carried out under sterile conditions.

Suitable metering systems are all devices which can produce discrete, uniform structures, e.g. drops, of predeterminable size.

If e.g. uncontrolled drop-formation devices are used, granules are obtained; when using suitable spray or atomization nozzles with metering pumps powders are preferably obtained as shaped articles.

Metering devices with nozzles, which eject the material to be converted to drops at regular intervals or intermittently, can furthermore be used for the process according to the invention.

An additionally preferred embodiment of the process according to the invention employs the Cryopel® process developed by Messer Griesheim GmbH (based on German Offenlegungsschrift 37 11 169). In conjunction with an immersion deep-freeze plant, the Cryope® plant, the conversion of the process according to the invention to the industrial scale is particularly simple in terms of apparatus. This plant, which can be operated with liquid nitrogen, is particularly distinguished by its economy. This plant is also suitable for sterile production. Continuous operation with low maintenance and cleaning expenditure makes possible the economical conversion of the process according to the invention to the industrial scale.

Figure 1:
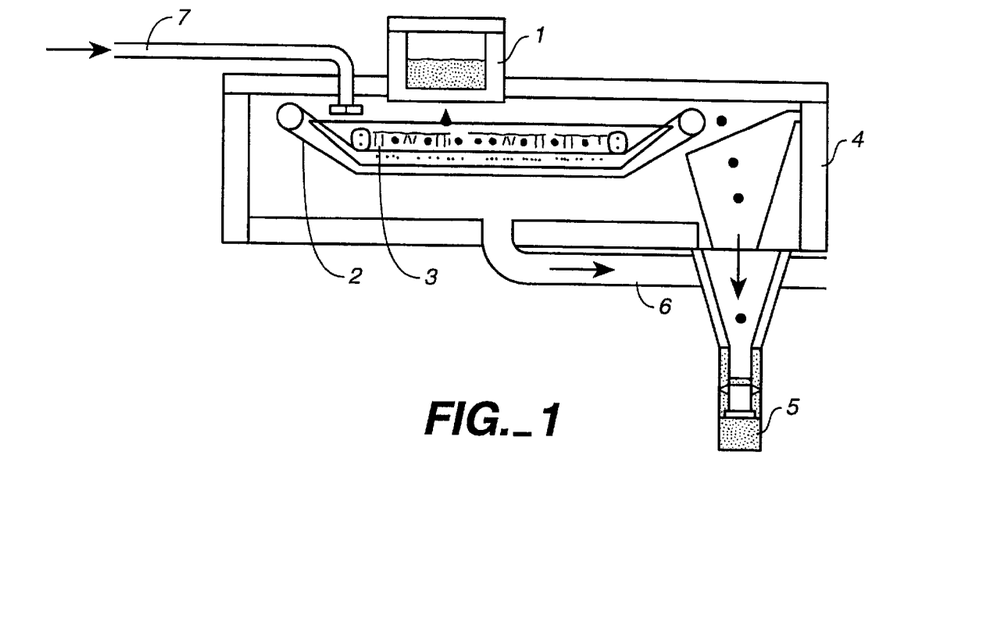
FIG. 1 shows: a schematic representation in cutaway view of a device for carrying out the process according to the invention.

The Cryopel® process developed by Messer Griesheim GmbH is shown schematically in FIG. 1. The matrix solution according to the invention, which contains the active compound in dissolved, emulsified or suspended form, is added dropwise to the liquid nitrogen bath 3 at −196° C. from the heatable entry device 1 via callibrated nozzles and shaped to give round pellets with simultaneous shock deep-freezing. By means of the conveyor belt 2 running continuously over deflecting rollers, the frozen product is discharged via the device 5. The metering of the liquid nitrogen is carried out by means of the supply line 7 and the resulting nitrogen gas escapes via the line 6. The insulation 4 encloses the entire system.

Figure 2:
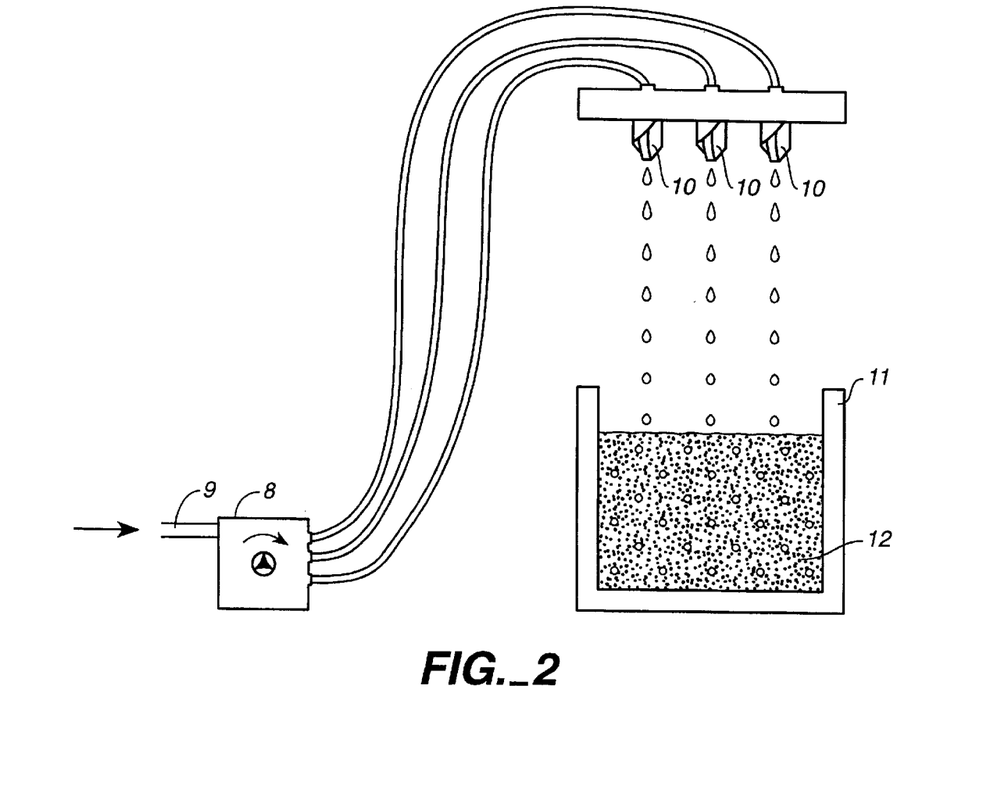
FIG. 2 shows: a further embodiment of a device for carrying out the process according to the invention in schematic representation.

FIG. 2 shows a schematic representation of a process in which the active compound matrix dispersion, which is cold or heated to at most 60° C., is added drop-wise continuously via the supply line 9 by means of the heatable drop nozzles 10 in the insulated trough 11 containing liquid nitrogen 12 by means of a controllable metering pump 8. The shock deep-frozen pellets are removed batchwise or continuously. Using this device highly viscous materials can be processed.

Should the system to be processed not be sufficiently capable of flow or drop formation, a further addition of water (e.g. of 1–10% by weight) can be carried out, the processing temperature can be increased or else even pressure can be used during the metering. In the converse case (system of too low viscosity), reduced pressure or temperature reduction is to be used analogously. In this manner uniform formation is guaranteed, as well as detachment of the individual drops.

The processing temperature can be varied within wide ranges, but in the case of thermolabile active compounds should be below 50° C.

Using the metering devices described, for example, materials whose viscosity varies within a wide range, e.g. $1\times10^{-3}$ to 12.5 Pa×s (Pascalseconds) and higher, can thus be metered without problems.

Further deep-cooled inert liquified gases which are suitable for the process according to the invention can be e.g. liquid rare gases such as argon.

Depending on the metering system selected, a grain size uniformity of over 80% can be achieved which can be even further increased by classification.

By classification of the frozen and separated portions, these can be converted into the liquid state once more and pelleted again so that a loss-free procedure is guaranteed.

In a preferred embodiment of the invention, the pellets are dried, two process variants resulting. Process variant A:

The shaped articles frozen at −196° C. (liquid nitrogen), e.g. pellets, are transferred to a freeze-drying plant. In this plant temperatures of 15° C. below the sublimation point of water are selected with a pressure of 0.1 Pa to $10^3$ Pa (0.001 to 1.03 mbar). The drying operation, which takes place in a conventional freeze-drying plant (condenser temperature −40° C.) at −25° C. and 33 Pa (0.33 mbar) in primary drying with sublimation of the water, frozen in amorphous form by the shock deep-freezing, from the matrix, leads after secondary drying (desorption) to a final product having a highly porous network. As a result of the shock deep-freezing according to the invention, the water is largely prevented from forming a crystalline phase, as a result of which a solid finely disperse amorphous water phase is formed in the matrix. After the sublimation of the water present in this way, highly porous micropore-containing networks are formed, which with respect to conventionally freezing processes have a distinctly increased surface area. Compared with conventionally freeze-dried materials, such pellets are particularly easily soluble and are preferably suitable for the development of instant preparations. Process variant B:

The frozen shaped articles, e.g. pellets, are thawed and conventionally dried. In this case it can be advantageous for accelerating the drying process and for keeping to low temperatures to work under vacuum (about 3,000–5,000 Pa (about 30–50 mbar)). Drying temperatures of up to 50° C. can be selected, the temperature during the drying process not rising above 30° C. in the pellet matrix as a result of the evaporation enthalpy of the liquid.

For conventionally dried pellets (process variant B) sol/gel-forming substances are necessary for the matrix which, in sol form, are capable of forming drops and after cryopelleting or after thawing form a gel which is stable after drying. Addition of plasticizers effects the matrix material with respect to consistency. Pellets prepared in this way are distinguished by particularly cost-effective preparation, as the lyophilization process step is not absolutely necessary.

Lipophilic active substances can be particularly advantageously processed without addition of further emulsifiers, e.g. using ultrasonic homogenizers when using types of gelatin and collagen hydrolyzates of high molecular weights, before further processing to stable emulsions or microemulsions.

Lipophilic/oily active compounds can be e.g.: garlic oil, cod-liver oil, vitamin E and further fat-soluble vitamins, hypericon oil, lecithin, juniper oil, omega-3-fatty acids, evening primrose oil, ethereal oils etc. With plant extracts whose active components exhibit both hydrophilic and lipophilic properties, the lipophilic components are first emulsified in the matrix material and the water-soluble constituents are dissolved in the hydrophilic matrix material and then cryopelleted.

Owing to the increased viscosity of the matrix system, active compounds present in suspended form can be prevented from sedimenting by simple stirring and simultaneously metered. Temperature-sensitive pharmaceutical substances are advantageously lyophilized.

The processing of the particular development forms of the invention indicated in the dependent claims such as e.g. formulations having controlled release or improved absorption, micro- and nanoencapsulation, precipitates, conjugate formation, film coatings and the preparation of pellets having bioadhesive properties is carried out according to the general sense of the description and in coordination with the particular active compound.

The process according to the invention itself can be carried out, looked at altogether, in a low maintenance and economical manner compared with the prior art. The cryopelleting, which is simple to carry out per se, surprisingly makes it possible clearly to surpass the prior art.

For carrying out the process according to the invention, it is sufficient in the simplest case to prepare an aqueous gelatin solution with a type of gelatin of the designated specification, to suspend the nifedipine or the dihydropyridine derivative homogeneously therein in finely crystalline form, and to add the system dropwise via a suitable metering device to an immersion bath containing liquid nitrogen. The deep-frozen pellets formed in this way are then converted to the dry state by lyophilization.

In the context of the present invention it has advantageously been shown that finely disperse dihydropyridine precipitates can also be produced directly in the gelatin solution by precipitation from a solution of the dihydropyridine in a water-miscible and pharmaceutically acceptable organic solvent, such as e.g. alcohol. After removal of the alcohol (e.g. by evaporation), a procedure analogous to the procedure described is used in order to prepare the shaped articles according to the invention.

For the combination preparations already mentioned, dihydropyridine derivatives can be combined, for example, with beta-sympathicolytics or diuretics.

In the case of optically active substances, both their racemates and the enantiomerically pure components and mixtures thereof can be employed.

Owing to the great breadth of variation of the invention, all pharmaceutical substances can be contained in the matrix materials described if they exhibit no incompatibilities with the individual constituents of the recipe materials. The term pharmaceutical substance here is defined according to the invention as follows:

Pharmaceutical substances can be of synthetic or natural origin, can be both chemically homogeneous substances or substance mixtures, and combinations of various pharmacologically active components. The term pharmaceutical substance, however, should further generally cover phytopharmaceuticals and plant extracts and finally also include hormones, vitamins and enzymes.

Enantiomerically pure active compounds or pseudo-racemates are also suitable according to the invention.

Active compounds from the dietetic foodstuffs sector (healthcare) and from the cosmetic sector can furthermore be used.

In the case of pharmaceutical substances suitable for the invention there is no limitation with respect to the indication groups whatsoever. In the following indication groups and some associated representatives are mentioned by way of example:

1. strong analgesics, e.g. morphine, dextropropoxyphen, pentazocine, pethidine, buprenorphine;
2. antirheumatics/anti-inflammatories (NSAR), e.g. indometacin, diclofenac, naproxen, ketoprofen, ibuprofen, flurbiprofen, acetylsalicylic acid, oxicams;
3. beta-sympathicolytics, e.g. propranolol, alprenolol, atenolol, bupranolol, salbutamol;
4. steroid hormones, e.g. betamethasone, dexamethasone, methylprednisolone, ethynylestradiol, medroxy-progesterone, prednisone, prednisolone;
5. tranquillizers, e.g. oxazepam, diazepam, lorazepam;
6. alpha-sympathicolytics, e.g. ergotamine, dihydroergotamine, dihydroergotoxin;
7. hypnotics and sedatives, e.g. secbutabarbital, secobarbital, pentobarbital, doxylamine, diphenhydramine;
8. tricyclic antidepressants, e.g. imipramine, nortriptyline, clomipramine, amitryptiline;
9. neuroleptics, e.g. chlorprothixen, chlorpromazine, haloperidol, triflupromazine;
10. antigout agents, e.g. benzbromarone, allopurinol;
11. antiparkinson agents, e.g. levodopa, amantadine;
12. coronary therapeutics or calcium antagonists, e.g. nifedipine and other dihydropyridine derivatives; nitric acid esters such as glycerol trinitrate, isosorbide mononitrate and isosorbide dinatrate; verapamil, gallopamil, molsidomine;
13. antihypertensives, e.g. clonidine, methyldopa, dihydralazine, diazoxide;
14. diuretics, e.g. mefruside, hydrochlorothiazide, furosemide, triamterene, spironolactone;
15. oral antidiabetics, e.g. tolbutamide, glibenclamide;
16. chemotherapeutics or antibiotics, e.g. penicillins such as phenoxymethylpenicillin, amoxycillin, ampicillin, pivampicillin, bacampicillin, dicloxacillin, flucloxacillin; cephalosporins such as cefalexin, cefaclor; gyrase inhibitors such as nalidixic acid, ofloxacin, norfloxacin; erythromycin, lincomycin, tetracycline, doxycycline, trimethoprim, sulfamethoxazole, chloramphenicol, rifampicin;
17. local anesthetics, e.g. benzocaine;
18. ACE inhibitors, e.g. enalapril, captopril;
19. mucolytics, e.g. acetylcysteine, ambroxole, bromhexine;
20. antiasthmatics, e.g. theophylline;
21. mineral preparations, e.g. magnesium, calcium or potassium salts, iron preparations;

22. neurotropics, e.g. piracetam;
23. ulcer therapeutics, e.g. cimetidine, pirenzepine;
24. provitamins and vitamins, e.g. biotin, cyanocobalamine, ergocalciferol, ascorbic acid, thiamine, pyridoxine, alpha-tocopherol, retinol, beta-carotene;
25. peptide pharmaceutical substances, e.g. insulin, interferons;
26. digitalis glycosides, e.g. digitoxin, digoxin;
27. antiemetics, e.g. metoclopramide;
28. enzymes, e.g. plasmin, deoxyribonuclease;
29. antiarrhythmics, e.g. prajmaline;
30. antiepileptics, e.g. phenytoin;
31. anticoagulants, e.g. phenprocoumon;
32. spasmolytics, e.g. papaverine;
33. antimycotics, e.g. clotrimazole;
34. hormones, e.g. calcitonin;
35. venotherapeutics, e.g. aescin;
36. immunosuppressants, e.g. cyclosporin;
37. tuberculostatics, e.g. rifampicin;
38. virustatics, e.g. aminoadamantane;
39. cytostatics, e.g. methotrexate;
40. vaccines, e.g. live poliomyelitis vaccine;
41. phytopharmaceuticals, e.g. Gingko biloba extract;
42. substances for the treatment of AIDS, such as e.g. renin antagonists;
43. calcium antagonists, such as dihydropyridine derivatives, in particular nifedipine, nitrendipine or nisoldipine.

Compared with the prior art, active compounds having poor tolerability or problematic bioavailability, and also light-, oxidation-, hydrolysis- and temperature-sensitive substances such as e.g. poorly soluble pharmaceutical substances, peptides, natural substances, enzymes, vitamins etc. can be processed particularly advantageously to give pharmaceutical forms according to the invention.

In order to explain the physiological background to the absorption of pharmaceutical substances in general and the improved absorption ratio of the pellet formulations according to the invention adequately, a consideration of the mechanism of the physiological absorption of pharmaceutical substances as is also presented in appropriate publications is initially necessary. However, the present invention is neither tied to the following attempt at a scientific explanation of the phenomena occurring according to the invention nor can it be restricted thereby.

Passive pharmaceutical substance absorption takes place according to the modern state of knowledge (theory according to Brodie et al.), if the following conditions exist:
 a) the gastrointestinal membrane acts as a lipid barrier,
 b) the pharmaceutical substance is only absorbed in dissolved and uncharged, i.e. nonionized form,
 c) acidic pharmaceutical substances are preferably absorbed in the stomach and basic pharmaceutical substances preferably in the intestine.

Figure 3:
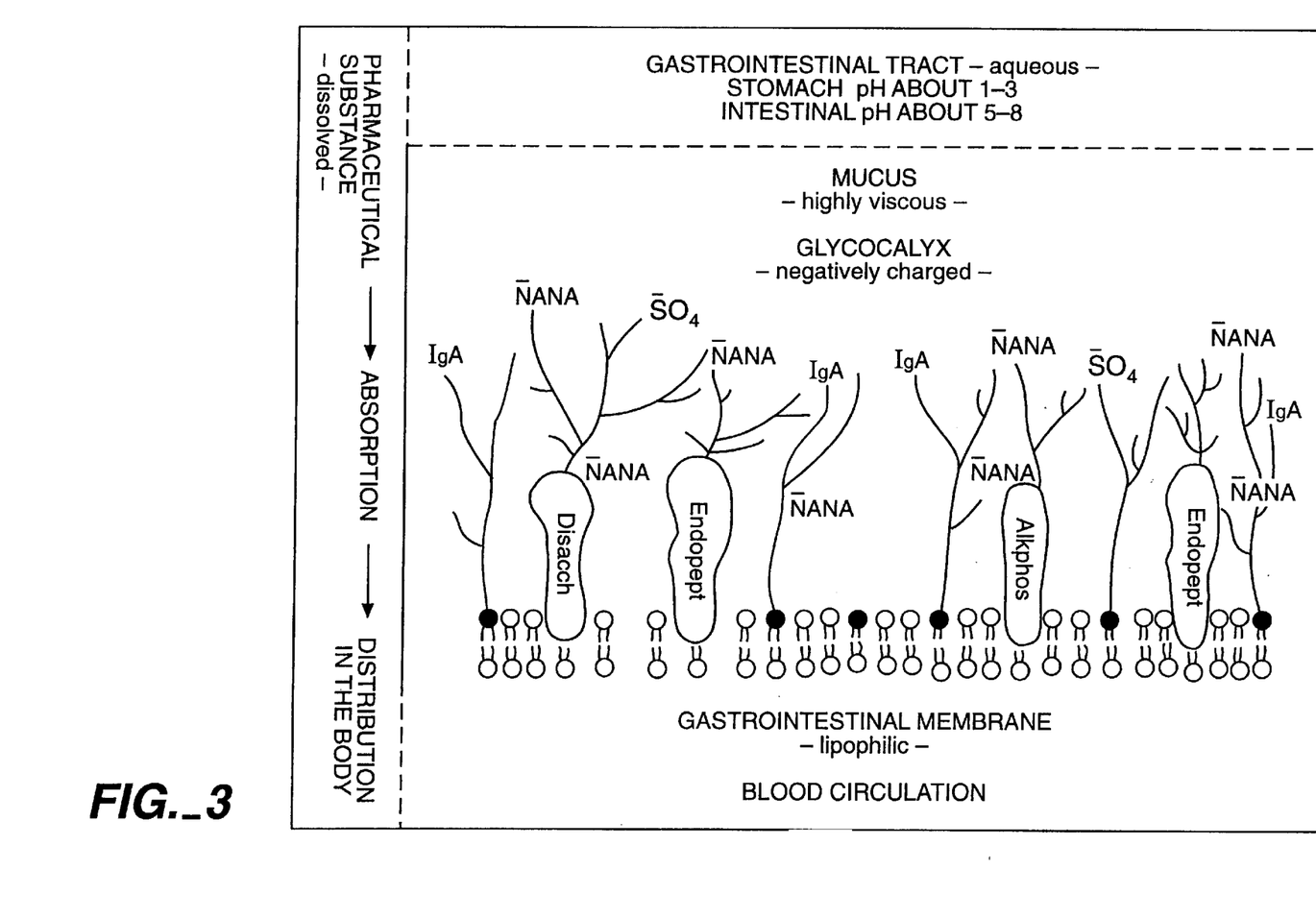
FIG. 3 shows: schematically the processes which take place during the passive absorption of pharmaceutical substances in the gastrointestinal membrane.

After the oral uptake of a pharmaceutical substance into the body, its absorption, i.e. the crossing into the general circulation (biophase) is hindered to a great degree by physical barriers (see FIG. 3), namely
 by the mucus layer and an aqueous layer adhering thereto
 the cell membranes of the intestinal epithelial cells with the glycocalyx covalently bonded thereto and
 the so-called "tight junctions" which connect the epithelial cells with one another on their apical sides.

These barriers presuppose that absorption of pharmaceutical substances takes place through the lipid bilayers fundamentally independently of their distribution mechanism and state of charge (so-called passive diffusion).

The epithelial cells of the entire gastro-intestinal tract are covered with a mucus layer which consists of mucins (glycoproteins), electrolytes, proteins and nucleic acids. In particular, the glyco-proteins form with the main component of the mucus, namely water, a viscous gel structure which primarily performs protective functions for the underlying epithelial layer. The mucus layer is bound to the apical surface of the epithelial cells via the glycocalyx. The glycocalyx likewise has a glycoprotein structure which is covalently bound to components of the membrane bilayer of the epithelial cells. The branched polysaccharides of the glycocalyx, which are either directly covalently bonded to amphiphilic molecules of the double membrane or to proteins incorporated in the double membrane, possess charged N-acetylneuraminic acid and sulfate radicals and are therefore negatively charged, which can lead to an electrostatic bond or repulsion of charged pharmaceutical substance molecules or of electrostatically charged particles. The epithelial cell membranes consist of phospholipid bilayers in which proteins are anchored via their hydrophobic regions. The phospholipid bilayers with their lipophilic content represent a further barrier for the transport of the pharmaceutical substances to be absorbed.

From this description, it clearly follows that charged pharmaceutical substance molecules or electro-statically charged particles therefore only have a very low chance of being absorbed via the oral administration route.

The shaped articles according to the invention for the first time provide the technical teaching to form a system with which these abovementioned absorption barriers can be overcome.

Hydrophilic macromolecules, in particular gelatin, are amphiphilic substances which, depending on the pH, have differing charge states. According to the invention, the hydrophilic macromolecule in the systems according to the invention can now be selected, or the pH of the formulation can be coordinated, such that a positive state of charge results in the physiological medium. At least a partial neutralization of the negative surface charges of the glycocalyx can thus be achieved. This neutralization phenomenon can become increasingly effective as a result of bioadhesive properties of the hydrophilic macromolecule, in particular gelatin.

As dissolved pharmaceutical substance molecules can now pass through the glycocalyx unhindered without being bound or repelled by electrostatic effects, they thus also reach the surface of the epithelial cells and are available there in a high concentration.

Active, carrier-mediated transport mechanisms or phagocytosis can now also make a substantial contribution to absorption.

The use of the powders, granules, or pellets according to the invention as shaped articles can be effected e.g. by means of customary dosage systems in hard gelatin capsules or as granules in sachets. As a result of the good flowability and approximately round shape of the granules, good meterability can be guaranteed. When using pellets the tightest sphere packing in exact coordination of the bulk volume to the -capsule size is possible, from which an improvement in dosage accuracy in the filling process results. Moreover, the addition of fillers can be dispensed with as a result of the appropriate selection of a certain pellet size.

The pellets having a size of 2–12 mm can be used according to the invention for a novel single-dose buccal, nasal or oral pharmaceutical form. Pellets employed orally are easily swallowable and can be sold in bottles with dosage dispensers in an environmentally compatible manner. In the case of buccal and nasal use, shaped article pellets with bioadhesive properties are suitable.

Powders, granules or pellets—as shaped articles—comprising matrix materials which dissolve rapidly and completely in cold water, can be used—filled into sachets—as instant preparations for the pharmaceutical or dietetic sector (healthcare).

Surprisingly, utilizing the bioadhesive properties of the sol/gel-forming agents, in particular gelatin, with the shaped articles according to the invention buccal and nasal formulations or pharmaceutical forms having pH-controlled release can be used.

A further use of these special granules or pellets as shaped articles is provided by their direct compressibility to give tablets. The tablets thus obtained surprisingly show, with low friability and high breaking strength, complete dissolution within 5 minutes, e.g. 2 minutes, measured according to customary test methods (e.g. dissolution test apparatus according to USP). Surprisingly, the good dissolving properties of the structural matrix are also retained after compressing. The tablets dissolve directly without advance disintegration. In contrast to this, tablets compressed from conventional granules always disintegrate first into granule particles, which only then dissolve.

Tablet preparation from freeze-dried shaped articles according to the invention is of importance, for example, in the design of a pharmaceutical form for temperature-sensitive active compounds. Because of their sensitivity (e.g. heat inactivation etc.) such pharmaceutical substances require particularly gentle processing processes, which advantageously can be very easily and simply ensured by the process according to the invention.

The application area for the shaped articles according to the invention is, of course, not only restricted to pharmaceutical purposes. Areas of use may also be in the biotechnological sector (cryopreservation of enzymes or bacteria, finished nutrient media in dried form etc.) and in the cosmetics sector (processing of plant extracts such as e.g. Aloe vera to give pellets offers the advantage of an ideal, dry transportation form for the moisture-sensitive extract and at the same time the naturally synthesized matrix system is particularly suitable as a constituent for ointments and creams).

Owing to the diverse variation and combination possibilities of the shaped articles according to the invention, the release of pharmaceutical substances in all intended uses indicated can be modulated within wide limits.

The following examples are intended to illustrate the invention in greater detail:

EXAMPLE 1

Pharmaceutical Substance: Benzocaine
Recipe of the Groundmass to be Processed:

| |
|---|
| 210 g of gelatin 170 Bloom |
| 50 g of dextran (molecular weight about 10,000) |
| 29 g of sucrose |
| 1 g of peppermint flavoring |
| 710 g of distilled water |
| 1000 g |

The gelatin powder is mixed with the peppermint flavoring, the water, which already contains the dextran and the sucrose in dissolved form, is added and after preliminary swelling at 50° C. the mixture is melted. 10 g of micronized benzocaine are suspended in this solution with ultrasonication.

The solution is then deaerated in vacuo. By means of the Cryopel metering device it is added dropwise to an immersion bath containing liquid nitrogen and pellets are thus formed.

The shock deep-frozen, round pellet shaped articles are dried in a freeze-drying unit with primary drying at −50° C. and 5 Pa (0.05 mbar) and secondary drying at 22° C.

78% of the pellets are in the size range from 0.8–1 mm. The dried pellets are compressed directly on an eccentric press to give a lozenge having an average benzocaine content of 5 mg.

EXAMPLE 2

Pharmaceutical Substance: Potassium Chloride
Recipe of the Groundmass to be Processed:

| |
|---|
| 625 g of collagen hydrolyzate (molecular weight 2,000–3,000 D) |
| 50 g of citric acid |
| 2325 g of distilled water |
| 3000 g |

The collagen hydrolyzate and the citric acid are dissolved in water with stirring. 190 g of potassium chloride are dissolved in this solution.

After defoaming in vacuo, the solution is added dropwise by means of the Cryopel metering device to an immersion bath containing liquid nitrogen and pellets of size of on average 4 mm are thus formed.

The water is removed as in example 1 by subsequent freeze-drying.

The pellets are packaged in air-tight sachets, corresponding to an individual dose of 1 g of potassium ions.

The contents of a sachet dissolve completely in water at room temperature within 30 sec.

EXAMPLE 3

Pharmaceutical Substance: Phenoxymethylpenicillin Potassium
Recipe of the Groundmass to be Processed:

200 g of dextran (molecular weight about 60,000)

200 g of collagen hydrolyzate (molecular weight 2,000–3,000)

5 g of orange flavoring 250 g of mannitol 100 g of sucrose

Distilled water to 2,500 g

The constituents are mixed and dissolved in the water. 100 g of phenoxymethylpenicillin potassium are dissolved in this solution with stirring.

After defoaming in vacuo, the solution is added dropwise by means of the Cryopel metering device to an immersion bath containing liquid nitrogen and pellets are thus formed. The water is removed by subsequent freeze-drying.

2.31 g of the dried pellets (corresponding to an average content of phenoxymethylpenicillin potassium of 270 mg) are used—sealed into individual sachets—as an instant beverage solution.

EXAMPLE 4

Example of a Matrix Material Comprising Gelatin and Plasticizer, in which Pharmaceutical Substance to be Processed can be Dissolved.

Gelatin 150 Bloom 2.6 kg

Spray-dried sorbitol 1.0 kg

Dihydrocodeine hydrogen tartrate 0.1 kg

Water 6.3 kg

The active compound is dissolved completely in 1 kg of water with stirring. The gelatin granules are preswollen in the remaining amount of water and dissolved at 40° C., and sorbitol and the active compound solution are then added with stirring. After melting the gelatin and homogenizing the solution, pellets as described in example 1 are prepared by dropwise addition of the material to liquid nitrogen. The pellets are dried in the customary manner at temperatures between 20° C. and 40° C. and then filled into opaque hard gelatin capsules having an average content of 10 mg of dihydrocodeine tartrate. In the dissolution test (apparatus according to USP XXI, 500 ml of water, 37° C., 50 rpm), the pharmaceutical form releases 70% of the active compound in 4.5 minutes.

The pellets obtained are transparently clear and lustrous.

EXAMPLE 5

Example of a Matrix Material Comprising Gelatin and Plasticizer, in which the Pharmaceutical Substance is Present in Emulsified Form.

Gelatin 210 Bloom 2.6 kg

Glycerol (85% strength) 1.25 kg

α-Tocopherol acetate 0.25 kg

Water 6.9 kg

The powdered gelatin is preswollen in cold water for 40 minutes and then dissolved at 50° C. Using an ultrasonic homogenizer, the active compound is emulsified in the gelatin solution at 50° C. The oil-in-water emulsion is then mixed with glycerol and cryopelletized. The pellets obtained are dried as in Example 4. The pellets are metered into opaque hard gelatin capsules containing 25 mg of α-tocopherol acetate.

The pellets obtained have an opaque and lustrous appearance.

EXAMPLE 6

Example for a Matrix Material Comprising Gelatin and Plasticizer, in which the Pharmaceutical Substance can be Suspended.

Gelatin 250 Bloom 2.5 kg

Glycerol (85% strength) 1.0 kg

Dexamethasone, micronized powder 0.025 kg

Water 4.0 kg

The soft gelatin material is preswollen in 1 kg of water and dissolved at 50° C. after addition of the remaining water. The active compound is homogeneously dispersed in this solution with stirring and the solution is then mixed with the glycerol. The suspension obtained is cryopelletized. After customary drying the pellets are filled into hard gelatin capsules having a steroid content of 0.5 mg.

The pellets obtained are transparent and lustrous.

EXAMPLE 7

Example of a Single-dose Pharmaceutical Form.

Mixture:

0.8 kg of gelatin 250 Bloom 0.8 kg of spray-dried sorbitol 0.8 kg of acetylsalicylic acid 1.6 kg of water The gelatin granules are preswollen for 30 minutes in the water and then dissolved at 70° C. The acetylsalicylic acid is dispersed in the solution obtained and the sorbitol is then added.

The matrix material obtained is added dropwise to liquid nitrogen by means of the apparatus shown in FIG. 2 at a temperature of the nozzles of 70° C. The shock deep-frozen pellets are classified with cooling and have a uniform size of 8 mm.

The round shaped articles are filled into a dose dispenser and—depending on the indication—can be administered individually.

Pellets prepared in this way are palatable and increase the tolerability, in particular in the case of cardiac infarct prophylaxis.

EXAMPLE 8

Production of an Ibuprofen Immediate-effect Pharmaceutical Form Based on Pellets.

Demonstration of the Increased Bioavailability.

Recipe:

400 g of ibuprofen USP XXII, micronized powder
400 g of gelatin powder 220 Bloom
1400 g of water The gelatin powder is preswollen for 45 min in the water and then dissolved at 60° C. The micronized ibuprofen is homogeneously dispersed in the gelatin solution and the resulting material is deaerated in vacuo.

The material is added dropwise to liquid nitrogen by means of the apparatus shown in FIG. 1 and pellets are thus formed. After drying at temperatures between 20° C. and 40° C. the pellets are filled into hard gelatin capsules containing 400 mg of ibuprofen.

In an in vivo human study, the immediate-effect form described was comparatively tested against a commercially available ibuprofen immediate-effect formulation which contains 600 mg of ibuprofen (in micronized form).

The following average plasma concentration-time values result, indicated in Ag of ibuprofen/ml of plasma.

| Time (h) | Formulation from Example 8 | Comparison preparation |
| --- | --- | --- |
| 1 | 27.5 | 5 |
| 2 | 35 | 19 |
| 2.5 | 37 | 23 |
| 3 | 35 | 22 |
| 5 | 17.5 | 15 |
| 7 | 8 | 6 |
| 9 | 5 | 5 |

EXAMPLE 9

Production of a Flurbiprofen Immediate-effect Pharmaceutical Form Based on Pellets, Demonstration of the Increased Bioavailability.

Recipe:

50 g of flurbiprofen, micronized powder 50 g of gelatin powder 220 Bloom 175 g of water The gelatin powder is preswollen for 45 min in the water and then dissolved at 60° C. The micronized flurbiprofen is homogeneously dispersed in the gelatin solution and the resulting material is deaerated in vacuo.

The material is added dropwise to liquid nitrogen by means of the apparatus shown in FIG. 1 and pellets are thus formed. After drying at temperatures between 20° C. and 40°

C. the pellets are filled into hard gelatin capsules containing 50 mg of flurbiprofen.

In an in vivo human study, the immediate-effect form described was comparatively tested against a commercially available flurbiprofen immediate-effect formulation which contains 50 mg of flurbiprofen (in micronized form).

The following average plasma concentration-time values result, indicated in gg of flurbiprofen/ml of plasma.

| Time (h) | Formulation from Example 9 | Comparison preparation |
| --- | --- | --- |
| 0.5 | 6.5 | 2 |
| 1 | 8 | 6 |
| 2 | 6 | 4.5 |
| 3 | 6 | 3.5 |
| 5 | 4.5 | 2 |

EXAMPLE 10

Pharmaceutical Substance: Nifedipine
Recipe of the Groundmass to be Processed:
  300 g of collagen hydrolyzate
  750 g of mannitol
  3950 g of distilled water The collagen hydrolyzate and the mannitol are dissolved in the dist. water with stirring. 100 g of micronized nifedipine are homogeneously suspended in this solution, if desired with addition of customary pharmaceutical auxiliaries. After defoaming under vacuum, the suspension is shaped to give pellets by dropwise addition at room temperature by means of the Cryopel® metering device to an immersion bath containing liquid nitrogen.

The water is removed by subsequent freeze-drying and round shaped articles are obtained, after classification, with an average nifedipine content of 2 mg.

These shaped articles disintegrate completely in water at room temperature (dissolution test apparatus according to USP, test medium 100 ml of water, 23° C.) within 20 seconds and release the amount of nifedipine contained.

The dried shaped articles are filled into a dark-colored dose container in which they are protected from entry of light and from which the desired dose can be removed.

EXAMPLE 11

The dried shaped articles from Example 10 are directly compressed in an eccentric press to give tablets having an average nifedipine content of 10 mg.

In a dissolution test apparutus according to USP (900 ml of 0.1 N HCl, paddle, 75 rpm, 37° C.), complete tablet dissolution and thus active compound release results within 5 minutes.

The pellets from Example 10 can alternatively be filled into opaque hard gelatin capsules having an average nifedipine content of 5 mg.

EXAMPLE 12

The recipe of the groundmass to be processed in Example 10 is altered as follows:
  300 g of collagen hydrolyzate
  60 g of polyvinylpyrrolidone K 15
  100 g of sucrose
  2540 g of distilled water The further working procedure is carried out analogously to Example 10.

The examples are only exemplary embodiments of the present invention. The person skilled in the art is accordingly also free to use or to prepare all pharmaceutical, cosmetic or other shaped articles according to the invention such as powders, granules, essentially symmetrical aggregates etc. if required within the scope of the present invention.

What is claimed is:

1. An active compound-containing powder, granule or pellet, comprising a dispersion of at least one active compound or active compound having poor absorbability in vivo in a matrix which essentially includes a structure-forming agent comprising hydrophilic macromolecules which are selected from the group consisting of collagen, gelatin, fractionated gelatin, collagen hydrolyzates, succinylated gelatin, plant proteins, plant protein hydrolyzates, elastin hydrolyzates, and mixtures thereof, which is prepared by a process that comprises the step of:
  a) dissolving a structure-forming agent comprising hydrophilic macromolecules selected from the group consisting of collagen, gelatin, fractionated gelatin, collagen hydrolyzates, succinylated gelatin, plant proteins, plant protein hydrolyzates, elastin hydrolyzates, in an aqueous or aqueous-organic solvent;
  b) dispersing the active compound and
  c) adding the mixture of dissolved structure-forming agent and dispersed active compound dropwise to a deeply-cooled, easily evaporable liquid and thus forming powders, granules or pellets, and
  d) drying the powders, granules or pellets thus formed by evaporation or sublimation of the solvent in a customary manner until the solvent is removed.

2. A powder, granule or pellet as claimed in claim 1, wherein the hydrophilic macromolecule is a thermoreversible sol/gel-forming agent.

3. A powder, granule or pellet as claimed in claim 1, wherein the matrix contains an additional structure-forming agent selected from the group consisting of: albumin, agar-agar, gum arabic, pectins, tragacanth, xanthan, natural and modified starches, dextrans, dextrins, maltodextrin, chitosan, alginates, cellulose derivatives, sugar, glycine, lactose, mannitol, polyvinylpyrrolidone, polyacrylic acid, polymers of methacrylic acid, polymers of methacrylic acid esters, cellulose acetate phthalate, hydroxypropylmethylcellulose phthalate, azo-crosslinked polymethacrylates, polyurethane/sugar copolymers, oligomeric galactomannans, galactomannan derivatives crosslinked with aliphatic diisocyanates, ethylgalactomannans, acetylgalactomannans, polysaccharides crosslinked with adipic acid, lipophilic substances, erodable fatty alcohols; and their mixtures.

4. A powder, granule or pellet as claimed in claim 3, wherein the active compound is a dihydropyridine derivative and the structure-forming agent includes hydrophilic macromolecules selected from the group consisting of: gelatin, fractionated gelatin, a gelatin derivative, collagen hydrolyzate or their mixture; and the additional structure-forming agent is selected from the group consisting of: dextran, sugar, glycine, lactose, sorbitol, mannitol, polyvinylpyrrolidone, and their mixtures.

5. A powder, granule or pellet as claimed in claim 1, wherein the matrix content of additional structure-forming agents is less than about 50% by weight.

6. A powder, granule or pellet as claimed in claim 1, comprising a pharmaceutically acceptable auxiliary or excipient for the matrix.

7. A powder, granule or pellet as claimed in claim 1, wherein it is present as a micropellet or an essentially symmetrical aggregate.

8. A powder, granule or pellet as claimed in claim 1, wherein it is present as a lyophilizate.

9. A powder, granule or pellet as claimed in claim 1, wherein
it is rapidly dissolving; and wherein the matrix includes a hydrophilic macromolecule selected from the group consisting of:
plant proteins, plant protein hydrolyzates, elastin hydrolyzates, collagen hydrolyzates, cold water-soluble gelatins, gelatin derivatives; having a maximum in the molecular weight distribution of below $10^5$ D.

10. A powder, granule or pellet as claimed in claim 1, wherein the matrix contains plasticizers and flavor correctants selected from the group consisting of:
glycerol, propylene glycol, polyethylene glycol, triacetin, sorbitol, sorbitan mixtures, glucose syrup; and their mixtures.

11. A powder, granule or pellet as claimed in claim 2, wherein the sol/gel-forming agent is a gelatin having a maximum in the molecular weight distribution above $10^5$ D.

12. A powder, granule or pellet as claimed in claim 11, wherein the active compound is selected from the group consisting of:
pharmaceutical substances of synthetic or natural origin, cosmetics, preventive agents, enzymes and microorganisms.

13. A powder, granule or pellet as claimed in claim 12, wherein the active compound is a dihydropyridine derivative.

14. A powder, granule or pellet as claimed in claim 13, wherein the dihydropyridine derivative is selected from the group consisting of: nifedipine, nitrendipine or nisoldipine.

15. A powder, granule or pellet as claimed in claim 12, wherein the active compound is present in dissolved, suspended, finely disperse, emulsified or microemulsified form or in the form of liposomes.

16. A powder, granule or pellet as claimed in claim 12, wherein the active compound is present as a conjugate with the hydrophilic macromolecule.

17. A powder, granule or pellet having controlled release as claimed in claim 1, wherein the matrix has a melting range of between about 35° C. and 40° C.

18. A powder, granule or pellet having controlled release as claimed in claim 17, wherein the matrix is present crosslinked with a pharmaceutically acceptable hardener selected from the group consisting of: aldoses and citral.

19. A powder, granule or pellet having controlled release as claimed in claim 17, wherein the shaped articles contain an additional hydrophilic macromolecule as a structure-forming agent or film coating, which is selected from the group consisting of: alginates, alginate-calcium phosphates, pectins, agar-agar, poly- and methacrylic acid derivatives, cellulose derivatives, cellulose acetate phthalate, hydroxypropylmethylcellulose phthalate, azo-crosslinked polymethacrylates, polyurethane/sugar copolymers, oligomeric galactomannans, galactomannan derivatives which are then crosslinked with aliphatic diisocyanates, galactomannan derivatives, ethyl galactomannans, acetylgalactomannan, polysaccharides crosslinked with adipic acid, lipophilic substances and erodable fatty alcohols.

20. A powder, granule or pellet as claimed in claim 12, wherein the matrix is present in covered form.

21. A nasal, buccal or oral pharmaceutical preparation containing powders, granules or pellets as claimed in claim 11.

22. A pharmaceutical preparation containing powders, granules or pellets as claimed in claim 1.

23. A cosmetic preparation containing powders, granules or pellets as claimed in claim 1.

24. A foodstuff preparation containing powders, granules or pellets as claimed in claim 1.

25. The process as claimed in claim 1 wherein the deeply-cooled easily evaporable liquid is liquid nitrogen.

26. A powder, granule or pellet as claimed in claim 3, wherein the lipophillic substances are selected from the group consisting of degradable monoglycerides, diglycerides, and triglycerides.

27. A powder, granule or pellet as claimed in claim 19 wherein the lipophillic substances are selected from the group consisting of degradable monoglycerides, diglycerides, and triglycerides.

* * * * *